(12) United States Patent
He et al.

(10) Patent No.: US 8,461,419 B2
(45) Date of Patent: Jun. 11, 2013

(54) PLANT HEIGHT REGULATORY GENE AND USES THEREOF

(75) Inventors: Zuhua He, Shanghai (CN); Yingying Zhang, Shanghai (CN); Qun Li, Shanghai (CN)

(73) Assignee: Shanghai Institutes for Biological Sciences, CAS, Shanghai (CN)

( * ) Notice: Subject to any disclaimer, the term of this patent is extended or adjusted under 35 U.S.C. 154(b) by 319 days.

(21) Appl. No.: 12/672,803

(22) PCT Filed: Aug. 11, 2008

(86) PCT No.: PCT/CN2008/071939
§ 371 (c)(1),
(2), (4) Date: Mar. 12, 2010

(87) PCT Pub. No.: WO2009/021448
PCT Pub. Date: Feb. 19, 2009

(65) Prior Publication Data
US 2011/0093966 A1     Apr. 21, 2011

(30) Foreign Application Priority Data
Aug. 10, 2007    (CN) .......................... 2007 1 0044772

(51) Int. Cl.
*C12N 15/87*   (2006.01)
*A01H 5/00*    (2006.01)
*A01H 1/00*    (2006.01)

(52) U.S. Cl.
USPC ........... 800/290; 800/278; 800/294; 800/298; 800/260; 800/320.1

(58) Field of Classification Search
None
See application file for complete search history.

(56) References Cited

U.S. PATENT DOCUMENTS

2005/0223428 A1* 10/2005 Torii et al. ................... 800/287
2007/0107083 A1*  5/2007 Poppenberger et al. ...... 800/287

FOREIGN PATENT DOCUMENTS

| CN | 1566146 A     | 1/2005 |
|----|---------------|--------|
| WO | 2006/023766 A2 | 3/2006 |
| WO | 2008/034648 A1 | 3/2008 |

OTHER PUBLICATIONS

Colliver et al (1997, Plant Mol. Biol. 35:509-522).*
Montgomery et al (Trends in Genetics, Jul. 1998, 14(7):255-258).*
Bowie et al, Science 247:1306-1310, 1990.*
McConnell et al, Nature 411 (6838):709-713, 2001.*
Exended European Search Report and Written Opinion dated Nov. 22, 2010, from the European Patent Office in related European Patent Application No. EP-08783932.0 (11 pages).
Database EMBL [Online], "Arabidopsis thaliana mRNA for cytochrome P45 like protein, complete cds, clone: RAFL09-95-E07"; Jul. 27, 2006, XP002609117, Database Accession No. AK227205. (2 pages).
International Search Report and Written Opinion dated Nov. 20, 2008, from The State Intellectual Property Office (SIPO) in related International Application No. PCT/CN2008/071939, with English translation. (19 pages).
Database EMBL [Online], Jul. 24, 2007, "Cytochrome P450 like protein, Arabidopsis thaliana (Mouse-ear cress), At5g24900" ; UniProtKB/TrEMBL Accession No. Q6NKZ8. (2 pages).
GenBank Accession No. BT012545, Apr. 23, 2004, Arabidopsis thaliana At5g24900 gene, complete cds. (2 pages).
GenBank Accession No. AF069716, Jan. 11, 2004, "Arabidopsis Thaliana BAC F6A4, Chromosome IV, near 60.5 cM, complete sequence; HTG; Arabidopsis thaliana (thale cress)". (27 pages).
Zhang, Y. Y., et al., "A Novel Mechanism of Inactivation of GA Regulated by Arabidopsis thaliana AtEui."; 2006 China Plant Cell Development and Molecular Biology Academic Symposium; Sep. 1, 2006 (1 page).
Zhang, Y.Y., et al., "The Discussion on Discovery and Application of a Novel GA Metabolic Pathway"; 2007 China Society of Plant Physiology National Academic Conference Collection of Paper Abstracts, Aug. 1, 2007 (1 page).
A Notification (Office Action) issued Feb. 10, 2011, by the Russian Patent Office in related Russian Patent Application No. 2010-108457/10(011943), with English translation (5 pages).
Examiner's First Report dated Feb. 16, 2011, issued by the Australian Patent Office in related Australian Patent Application No. 2008-286583 (4 pages).
Official Action issued Oct. 10, 2011, by the Russian Patent Office in related Russian Patent Application No. 2010-108457/10, with English translation (7 pages).
Database EMBL (online), Jul. 24, 2007, "Cytochrome P450 like protein, Arabidopsis thaliana (Mouse-ear cress), At5g24900"; UniProtKB/TrEMBL Accession No. Q6NKZ8. (2 pages).
GenBank AccessionNo. BT012545, Apr. 23, 2004, "Arabidopsis thaliana At5g24900 gene", complete cds. (2 pages).
GenBank Accession No. AF069716, Jan. 11, 2004, "Arabidopsis Thaliana BAC F6A4, Chromosome IV, near 60.5 cM, complete sequence; HTD; Arabidopsis thaliana (thale cress)". (27 pages).
Luo, Anding, et al., "EUI1, Encoding a Putative Cytochrome P450 Monooxygenase, Regulates Internode Elongation by Modulating Gibberellin Responses in Rice"; Plant Cell Physiol. 47(2): 181-191 (2006).
Official Action issued Jun. 15, 2011, by the Russian Patent Office in related Russian Patent Application No. 2010108457, with English translation (9 pages).
GenBank Accession No. BT011240.1, "Arabidopsis thaliana At5g24900 gene, complete cds"; Jan. 14, 2004, [retrieved on Nov. 2, 2008]; Retrieved from: GenBank Database. (3 pages).
Zhu, Yongyou, et al., "Elongated Uppermost Internode Encodes a Cytochrome P450 Monooxygenase That Epoxidizes Gibberellins in a Novel Deactivation Reaction in Rice"; American Society of Plant Biologists, The Plant Cell, vol. 18, Feb. 2006; pp. 442-456.

(Continued)

*Primary Examiner* — Stuart F Baum
(74) *Attorney, Agent, or Firm* — Osha Liang LLP

(57) ABSTRACT

Provided are a crop height regulatory gene from *Arabidopsis thaliana*, expression regulatory sequences thereof and uses thereof. The crop regulatory gene can be used to regulate the plant height, volume, tiller, yield, flower organ size, or seed size of crops.

12 Claims, 2 Drawing Sheets

OTHER PUBLICATIONS

Notice of Reasons for Rejection (Office Action) issued Aug. 29, 2012, by the Japan Patent Office in related Japanese Patent Application No. JP-2010-519332, with English translation (14 pages).

Communication pursuant to Article 94(3) EPC (Office Action) issued Jul. 19, 2012, by the European Patent Office in related European Patent Application No. 08 783 932.0-1212 (3 pages).

Examiner's Requisition dated Feb. 13, 2012, issued by the Canadian Intellectual Property Office in related Canadian Patent Application No. 2,695,929 (4 pages).

Official Action dated Nov. 2, 2012, from the Department of State Enterprise "Ukranian Institute of Industrial Property", in related Ukranian Patent Application No. 2010-02637, with partial English translation (12 pages).

Notice of Decision of Rejection (Office Action) dated Oct. 26, 2012, from the Korean Intellectual Property Office for related Korean Patent Application No. 10-2010-7005199, with English translation (6 pages).

Korean Office Action dated Jan. 20, 2012 for related Korean Application No. 10-2010-7005199, with English translation (13 pages).

* cited by examiner

SEQUENCE LISTING

<160> NUMBER OF SEQ ID NOS: 13

<210> SEQ ID NO 1
<211> LENGTH: 3040
<212> TYPE: DNA
<213> ORGANISM: Arabidopsis thaliana

<400> SEQUENCE: 1

```
aagaagtgaa gatgcaaata aaataaaaag taaaagatcc tgaatagaca aaaagttaaa      60
atggagagtt tggttgttca tacggtaaat gcaatttggt gcatagttat tgtcggaatc     120
ttcagcgtag gttatcatgt gtatggaaga gcggtggtgg agcagtggag gatgcggagg     180
agtttaaagt tgcaaggcgt gaagggtcct ccaccgtcga tctttaacgg caatgtgtcg     240
gagatgcaac ggattcagtc ggaggctaaa cactgttccg gcgataacat catttctcat     300
gactattctt cttctctatt tcctcatttc gatcactggc gaaaacaata cggtttgttt     360
tttaaatctc gtttagtaca aaatgcatac atataacaat atcaaaaaat tcatttaaat     420
cgtaaactag aacaacattt ataaatctat taactacata tgaagtttca tttacacagt     480
ttttaagttt atgggtttga tattcgagcc atatcatcgc attaaaaaca aaaaaatccc     540
aaatgcacta gtggttaaaa gattaaaaaa aatatattgt ttttgatag agttcaaact      600 ttttcattat gatttcaatt atcttggctt ctcatacatt ttaaataata aatccttcaa     660
tttttatgga tttagaggt acttatcatt tcaacttagg ttttgaatgg atcttgtggt     720
tagtgcggac taatccgtca gcggtgtaat ccatattatt tttggggcgg acaacaaagc     780
gctgtggatt tagtctaaag acaatccaca gttagtgtgt agtgttttt ttttgttttt      840 ttttagtccc aatattaaaa actataattt atgaatggta aataaaaagc gatccggttt     900
gtaaatgtta ttattcgttt ggaccgctgt aaccattcaa aagtttctca aaaaaaactt     960
atacattttt attagaaaat tattgttcaa aagttaatgt tcttcatagt agggtccatc    1020
ccacttaaaa ggcattgaac gtttcacttg cattcacaaa aagacagctt tgcaagcttt    1080
ttctcagtta acgttacacg aagaaaaatc cattaccaga tagaagaaaa tatcccatca    1140
aagacaacac atatatagaa taaaaatgta gaaacgtctg catataggtt attctaaatt    1200
aattagagaa atatgatcca cgcacatatt tacttaattg aattcaatac aaataaaagt    1260
tgtgcatgag catgatgatt gtgatttggg cgtggctgaa cttgaaccaa gtttgatatt    1320
ggtttggagt aatttttttt taatacaaaa cggtaatgaa ggaaggattt acacatactc    1380
aacggggtta aagcagcacc tttacataaa ccacccggaa atggtgaagg agcttagcca    1440
aaccaacaca cttaaccttg gtagaatcac tcacatcacc aaacgcctta accccattct    1500
cggcaatggc atcatcacct ctaatgggcc tcattgggcc catcaacgtc gtatcattgc    1560
ctatgagttt acccacgaca aaatcaaggt tctattcaca ttgcgaacta attaaagata    1620
```

```
tggatgtaga aatcttaata tatatattga tttgaaatat tgttgtgatt gcctgattgg    1680
tgaatggtga agggaatggt tggtttaatg gtggaatctg ccatgccaat gttgaacaaa    1740
tgggaagaga tggtgaaaag aggaggagaa atggggttgtg acataagagt ggacgaagac   1800
cttaaggatg tctcagctga tgtcatcgct aaggcttgct ttgggagctc ttttcaaaa    1860 ggcaaagcaa tattctctat gattagggat cttttaaccg ccattactaa acgaagcgtc   1920
ctcttcagat tcaatggctt cacgtaagtt tcgatatatt tatttttct acttcttcca    1980 tgcaaaacta tttctctata taatatagtt gagtatacgg tggcaagtga tatggtgttt   2040
ggaagtaaga agcatggtga tgtggatatt gatgcgcttg agatggaatt agaatcttct   2100
atatgggaaa cggttaagga gagggaaatt gaatgtaagg atactcacaa gaaggatcta   2160
atgcagttga tactcgaggg agcgatgcga agctgcgatg gtaacttgtg ggacaagtca   2220
gcctatagac ggtttgtggt ggacaattgc aagagcatct atttcgccgg acatgattca   2280
accgcagtct cagtgtcttg gtgccttatg ctcctcgctc tcaatcctag ttggcaggtt   2340
aaaattcgcg atgaaatctt gagttcttgc aagaatggca ttcccgacgc agaatcaatt   2400
cctaatctca aaacggtaat cttttattta taatcataaa gaaaacgtta gagaatttta   2460
cattgaatga atttatacac aaaatcagtg tataaatgta gcttatttta aaaatctaac   2520
aacattttat tgttaatata tataaatgtt ataaaatagg tgacaatggt aatcaagaa    2580 acaatgagac tatacccacc agcaccaatc gtgggaagag aagcatccaa agacataaga   2640
cttggagacc ttgtggtgcc aaaaggagtg tgcatttgga cactcattcc tgccttacac   2700
cgagaccccg agatctgggg accagacgca aacgacttca gccagagag gtttagtgag   2760 ggaatctcta aggcttgcaa ataccctcag tcatacatcc catttggcct tggaccaaga   2820
acatgcgtag gcaaaaactt tggtatgatg gaagtgaaag tgcttgtttc acttattgtc   2880
tcaaagttca gttttactct ttccccgact tatcagcact ctccaagcca taaactcctt   2940
gtagagcctc aacatggtgt tgtcattagg gttgttttgac tgtgttacgt gatccgtaga   3000
cttttataat gatttaattt gctttgtgtg ttcgaatttc                          3040
```

<210> SEQ ID NO 2
<211> LENGTH: 1578
<212> TYPE: DNA
<213> ORGANISM: Arabidopsis thaliana

<400> SEQUENCE: 2

```
atggagagtt tggttgttca tacggtaaat gcaatttggt gcatagttat tgtcggaatc     60
ttcagcgtag gttatcatgt gtatggaaga gcggtggtgg agcagtggag gatgcggagg   120
agtttaaagt tgcaaggcgt gaagggtcct ccaccgtcga tctttaacgg caatgtgtcg   180
gagatgcaac ggattcagtc ggaggctaaa cactgttccg gcgataacat catttctcat   240
gactattctt cttctctatt tcctcatttc gatcactggc gaaaacaata cggaaggatt   300
tacacatact caacgggggtt aaagcagcac ctttacataa accacccgga aatggtgaag   360
gagcttagcc aaaccaacac acttaacctt ggtagaatca ctcacatcac caaacgcctt   420
aaccccattc tcggcaatgg catcatcacc tctaatgggc ctcattgggc ccatcaacgt   480
cgtatcattg cctatgagtt tacccacgac aaaatcaagg gaatggttgg tttaatggtg   540
gaatctgcca tgccaatgtt gaacaaatgg aagagatgg tgaaagagg aggaaaatg     600 ggttgtgaca taagagtgga cgaagacctt aaggatgtct cagctgatgt catcgctaag   660
gcttgctttg ggagctcttt ttcaaaaggc aaagcaatat tctctatgat tagggatctt   720
```

```
ttaaccgcca ttactaaacg aagcgtcctc ttcagattca atggcttcac tgatatggtg    780
tttggaagta agaagcatgg tgatgtggat attgatgcgc ttgagatgga attagaatct    840
tctatatggg aaacggttaa ggagagggaa attgaatgta aggatactca caagaaggat    900
ctaatgcagt tgatactcga gggagcgatg cgaagctgcg atggtaactt gtgggacaag    960
tcagcctata gacggtttgt ggtggacaat gcaagagca tctatttcgc cggacatgat   1020
tcaaccgcag tctcagtgtc ttggtgcctt atgctcctcg ctctcaatcc tagttggcag   1080
gttaaaattc gcgatgaaat cttgagttct tgcaagaatg gcattcccga cgcagaatca   1140
attcctaatc tcaaaacggt gacaatggta atacaagaaa caatgagact atacccacca   1200
gcaccaatcg tgggaagaga agcatccaaa gacataagac ttggagacct tgtggtgcca   1260
aaaggagtgt gcatttggac actcattcct gccttacacc gagaccccga gatctgggga   1320
ccagacgcaa acgacttcaa gccagagagg tttagtgagg aatctctaa ggcttgcaaa   1380 taccctcagt catacatccc atttggcctt ggaccaagaa catgcgtagg caaaaacttt   1440
ggtatgatgg aagtgaaagt gcttgtttca cttattgtct caaagttcag ttttactctt   1500
tccccgactt atcagcactc tccaagccat aaactccttg tagagcctca acatggtgtt   1560
gtcattaggg ttgtttga                                                1578

<210> SEQ ID NO 3
<211> LENGTH: 525
<212> TYPE: PRT
<213> ORGANISM: Arabidopsis thaliana

<400> SEQUENCE: 3

Met Glu Ser Leu Val Val His Thr Val Asn Ala Ile Trp Cys Ile Val
1               5                   10                  15

Ile Val Gly Ile Phe Ser Val Gly Tyr His Val Tyr Gly Arg Ala Val
                20                  25                  30

Val Glu Gln Trp Arg Met Arg Arg Ser Leu Lys Leu Gln Gly Val Lys
            35                  40                  45

Gly Pro Pro Pro Ser Ile Phe Asn Gly Asn Val Ser Glu Met Gln Arg
        50                  55                  60

Ile Gln Ser Glu Ala Lys His Cys Ser Gly Asp Asn Ile Ile Ser His
65                  70                  75                  80

Asp Tyr Ser Ser Ser Leu Phe Pro His Phe Asp His Trp Arg Lys Gln
                85                  90                  95

Tyr Gly Arg Ile Tyr Thr Tyr Ser Thr Gly Leu Lys Gln His Leu Tyr
            100                 105                 110

Ile Asn His Pro Glu Met Val Lys Glu Leu Ser Gln Thr Asn Thr Leu
        115                 120                 125

Asn Leu Gly Arg Ile Thr His Ile Thr Lys Arg Leu Asn Pro Ile Leu
    130                 135                 140

Gly Asn Gly Ile Ile Thr Ser Asn Gly Pro His Trp Ala His Gln Arg
145                 150                 155                 160

Arg Ile Ile Ala Tyr Glu Phe Thr His Asp Lys Ile Lys Gly Met Val
                165                 170                 175

Gly Leu Met Val Glu Ser Ala Met Pro Met Leu Asn Lys Trp Glu Glu
            180                 185                 190

Met Val Lys Arg Gly Gly Glu Met Gly Cys Asp Ile Arg Val Asp Glu
        195                 200                 205

Asp Leu Lys Asp Val Ser Ala Asp Val Ile Ala Lys Ala Cys Phe Gly
    210                 215                 220
```

Ser Ser Phe Ser Lys Gly Lys Ala Ile Phe Ser Met Ile Arg Asp Leu
225                 230                 235                 240

Leu Thr Ala Ile Thr Lys Arg Ser Val Leu Phe Arg Phe Asn Gly Phe
            245                 250                 255

Thr Asp Met Val Phe Gly Ser Lys Lys His Gly Asp Val Asp Ile Asp
        260                 265                 270

Ala Leu Glu Met Glu Leu Glu Ser Ser Ile Trp Glu Thr Val Lys Glu
    275                 280                 285

Arg Glu Ile Glu Cys Lys Asp Thr His Lys Lys Asp Leu Met Gln Leu
    290                 295                 300

Ile Leu Glu Gly Ala Met Arg Ser Cys Asp Gly Asn Leu Trp Asp Lys
305                 310                 315                 320

Ser Ala Tyr Arg Arg Phe Val Val Asp Asn Cys Lys Ser Ile Tyr Phe
            325                 330                 335

Ala Gly His Asp Ser Thr Ala Val Ser Val Ser Trp Cys Leu Met Leu
        340                 345                 350

Leu Ala Leu Asn Pro Ser Trp Gln Val Lys Ile Arg Asp Glu Ile Leu
    355                 360                 365

Ser Ser Cys Lys Asn Gly Ile Pro Asp Ala Glu Ser Ile Pro Asn Leu
370                 375                 380

Lys Thr Val Thr Met Val Ile Gln Glu Thr Met Arg Leu Tyr Pro Pro
385                 390                 395                 400

Ala Pro Ile Val Gly Arg Glu Ala Ser Lys Asp Ile Arg Leu Gly Asp
            405                 410                 415

Leu Val Val Pro Lys Gly Val Cys Ile Trp Thr Leu Ile Pro Ala Leu
        420                 425                 430

His Arg Asp Pro Glu Ile Trp Gly Pro Asp Ala Asn Asp Phe Lys Pro
    435                 440                 445

Glu Arg Phe Ser Glu Gly Ile Ser Lys Ala Cys Lys Tyr Pro Gln Ser
    450                 455                 460

Tyr Ile Pro Phe Gly Leu Gly Pro Arg Thr Cys Val Gly Lys Asn Phe
465                 470                 475                 480

Gly Met Met Glu Val Lys Val Leu Val Ser Leu Ile Val Ser Lys Phe
            485                 490                 495

Ser Phe Thr Leu Ser Pro Thr Tyr Gln His Ser Pro Ser His Lys Leu
        500                 505                 510

Leu Val Glu Pro Gln His Gly Val Val Ile Arg Val Val
    515                 520                 525

<210> SEQ ID NO 4
<211> LENGTH: 2778
<212> TYPE: DNA
<213> ORGANISM: Arabidopsis thaliana

<400> SEQUENCE: 4
agtgctcgac tatacatata gccaagaag agcagaaaaa tcaaagtcgt gagttcagaa      60
gctataacaa aatttctaag aaaagaaag ataagaaaat ggagaatttt atggtagaga     120
tggccaagac catttcgtgg atagttgtaa taggagtgtt aggtttaggg attcgtgttt     180
acggtaaagt gatggcggag caatggagga tgcggaggaa gctgacgatg cagggcgtga     240
agggtcctcc gccgtcgcta tttcgtggaa acgtgccgga gatgcaaaaa atccagtcac     300
aaataatgag taactctaaa cactactccg gtgataatat catcgcccat gactacactt     360
cttctctctt tccatatctc gaccactggc gaaaacaata cggtaagctt tcaataatct     420

```
gataatttca acaattttg agactcttaa ttttgggatc tgtggcaaat gttttttgt      480 caacaaagta gatacgcctc tgaatttgaa taatgatagc acacaaggca gattagtcct    540
ttgttggtcg ttttgagtta gacgaatcca tttttcggac cgatgatgat gcagacaaaa    600
caaacatata tcttcattaa atcttgtaaa tagttaacga aagtactata tcattacaca    660
cacatacaaa agacactagt taacatgcat acgtgaattt atatattcat aatacatgcg    720
tgaattttaa ttcatacata tgtgaatact gattgacagc taagtcgtat atataatata    780
tgtgtgtaac gtatgcatgg attgacatga cacctaatga caactaacgc cgcagaattt    840
aaaatttatg aaaagccaat aaggttttgt acgatcgggt ctacttgatc caaaagttag    900
gagctgatca attatatgat aactcctcaa tgattcattt tgattccctt tttttatag     960 taataaatcg taagatatat tttaaattta gttttaaaat accaaagtag ttgtcgcttc    1020
gctagtggat cgtttaatag tttatgatcg gtcatattga ttgagaggaa atcttaagtt    1080
tttgattttc accgttttct aagttggttt tgagcattta ttgtatattt attttgtatg    1140
agtaatttat tgaaaaaaat tgatatgttc agggagagtg tacacgtatt cgacggggt     1200 gaagcaacac ttgtacatga accacccgga gttggtgaaa gaacttaacc aagccaacac    1260
tcttaacctt ggcaaagtct cttacgtcac caaacgcctt aaatccattc ttggccgtgg    1320
tgttatcacc tctaatgggc tcattgggc ccatcaacgt cgtatcattg cacctgagtt     1380
tttcctcgac aaagtcaagg gaatggtggg attggtggtg gaatcagcga tgccaatgct    1440
gagtaaatgg gaagagatga tgaaaagaga aggagaaatg gtgtgtgaca taattgtaga    1500
cgaagaccta agagctgcct ctgctgacgt tatctctaga gcttgctttg ggagctcttt    1560
ctccaaaggc aaagagatct tctctaagct tagatgtctt caaaaggcca tcactcacaa    1620
caacatcctc ttcagcctca atggcttcac gtaagtgaat tcaaaagtca tttctatctc    1680
tatatatatt ttattaaggc agtgtcatgt aatggtgtta aattttgtgg ttgcaagtga    1740
tgttgtgttc gggactaaga agcatgggaa cgggaagatt gatgagctag agagacacat    1800
tgagtctttg atatgggaaa ccgttaaaga aagagaaagg gaatgtgtgg gagatcacaa    1860
gaaggatcta atgcagttga tactagaagg ggccaggagt agttgtgatg gcaacttgga    1920
ggacaagaca caatcttaca aaagtttcgt ggtggacaat tgcaagagca tctattttgc    1980
cgggcatgag accagtgcgg ttgctgtctc ttggtgtctt atgctcctcg ctctcaaccc    2040
ttcttggcaa actcgtatcc gcgatgaagt ctttcttcat tgcaagaacg gtatacctga    2100
cgcagactct atttccaacc tcaaaacggt aatttacaag ttacaacctt gcctctcatg    2160
tcaagttcct taaactctct taaaccaaaa aaaaaatgt tccttggact ccaagtatga     2220
ctattttcat aacctaacat cacttgaata aaaatatagg tgacaatggt tatccaggaa    2280
acgttgaggc tatacccacc agcagcattc gtgtcgagag aagcccttga ggacacaaaa    2340
ctcggaaacc tcgtggtgcc aaagggagtg tgcatctgga cgttgatccc tacattgcac    2400
agagaccctg agatatgggg agctgacgca aatgaattca atccagaaag atttagcgaa    2460
ggagtctcta aagcctgcaa acaccctcag tcattcgtcc catttggctt agggacaagg    2520
ttgtgtttag gaaagaattt ggtatgatg gagctcaagg ttcttgtctc acttattgtg      2580
tcaaggttta gctttactct ctctcccaca tatcaacact ctccggtgtt tagaatgctt    2640
gtagagcctc aacatggtgt tgtcattaga gttctgagac aataagatat gtcgttagct    2700
tatggtttta gttttaatcc tgtgtaataa taagatatta ttacactata gtactataat    2760
agtatttcct ttggtatc                                                  2778
```

<210> SEQ ID NO 5
<211> LENGTH: 1599
<212> TYPE: DNA
<213> ORGANISM: Arabidopsis thaliana

<400> SEQUENCE: 5

| | | |
|---|---|---|
| atggagaatt ttatggtaga gatggccaag accatttcgt ggatagttgt aataggagtg | 60 |
| ttaggtttag ggattcgtgt ttacggtaaa gtgatggcgg agcaatggag gatgcggagg | 120 |
| aagctgacga tgcagggcgt gaagggtcct ccgccgtcgc tatttcgtgg aaacgtgccg | 180 |
| gagatgcaaa aaatccagtc acaaataatg agtaactcta acactactc cggtgataat | 240 |
| atcatcgccc atgactacac ttcttctctc tttccatatc tcgaccactg gcgaaaacaa | 300 |
| tacgggagag tgtacacgta ttcgacgggg gtgaagcaac acttgtacat gaaccacccg | 360 |
| gagttggtga agaacttaa ccaagccaac actcttaacc ttggcaaagt ctcttacgtc | 420 |
| accaaacgcc ttaaatccat tcttggccgt ggtgttatca cctctaatgg gcctcattgg | 480 |
| gcccatcaac gtcgtatcat tgcacctgag tttttcctcg acaaagtcaa gggaatggtg | 540 |
| ggattggtgg tggaatcagc gatgccaatg ctgagtaaat gggaagagat gatgaaaaga | 600 |
| gaaggagaaa tggtgtgtga cataattgta gacgaagacc taagagctgc ctctgctgac | 660 |
| gttatctcta gagcttgctt tgggagctct ttctccaaag gcaaagagat cttctctaag | 720 |
| cttagatgtc ttcaaaaggc catcactcac aacaacatcc tcttcagcct caatggcttc | 780 |
| actgatgttg tgttcgggac taagaagcat gggaacggga agattgatga gctagagaga | 840 |
| cacattgagt ctttgatatg ggaaaccgtt aaagaaagag aaagggaatg tgtgggagat | 900 |
| cacaagaagg atctaatgca gttgatacta aaggggcca ggagtagttg tgatggcaac | 960 |
| ttggaggaca agacacaatc ttacaaaagt ttcgtggtgg acaattgcaa gagcatctat | 1020 |
| tttgccgggc atgagaccag tgcggttgct gtctcttggt gtcttatgct cctcgctctc | 1080 |
| aacccttctt ggcaaactcg tatccgcgat gaagtctttc ttcattgcaa gaacggtata | 1140 |
| cctgacgcag actctatttc caacctcaaa acggtgacaa tggttatcca ggaaacgttg | 1200 |
| aggctatacc caccagcagc attcgtgtcg agagaagccc ttgaggacac aaaactcgga | 1260 |
| aacctcgtgg tgccaaaggg agtgtgcatc tggacgttga tccctacatt gcacagagac | 1320 |
| cctgagatat ggggagctga cgcaaatgaa ttcaatccag aaagatttag cgaaggagtc | 1380 |
| tctaaagcct gcaaacaccc tcagtcattc gtcccatttg cttagggaca aggttgtgt | 1440 |
| ttaggaaaga attttggtat gatggagctc aaggttcttg tctcacttat tgtgtcaagg | 1500 |
| tttagcttta ctctctctcc cacatatcaa cactctccgg tgtttagaat gcttgtagag | 1560 |
| cctcaacatg gtgttgtcat tagagttctg agacaataa | 1599 |

<210> SEQ ID NO 6
<211> LENGTH: 532
<212> TYPE: PRT
<213> ORGANISM: Arabidopsis thaliana

<400> SEQUENCE: 6

Met Glu Asn Phe Met Val Glu Met Ala Lys Thr Ile Ser Trp Ile Val
1               5                   10                  15

Val Ile Gly Val Leu Gly Leu Gly Ile Arg Val Tyr Gly Lys Val Met
                20                  25                  30

Ala Glu Gln Trp Arg Met Arg Arg Lys Leu Thr Met Gln Gly Val Lys
            35                  40                  45

Gly Pro Pro Pro Ser Leu Phe Arg Gly Asn Val Pro Glu Met Gln Lys

-continued

```
             50                  55                  60
Ile Gln Ser Gln Ile Met Ser Asn Ser Lys His Tyr Ser Gly Asp Asn
 65                  70                  75                  80
Ile Ile Ala His Asp Tyr Thr Ser Ser Leu Phe Pro Tyr Leu Asp His
                 85                  90                  95
Trp Arg Lys Gln Tyr Gly Arg Val Tyr Thr Tyr Ser Thr Gly Val Lys
                100                 105                 110
Gln His Leu Tyr Met Asn His Pro Glu Leu Val Lys Glu Leu Asn Gln
                115                 120                 125
Ala Asn Thr Leu Asn Leu Gly Lys Val Ser Tyr Val Thr Lys Arg Leu
            130                 135                 140
Lys Ser Ile Leu Gly Arg Gly Val Ile Thr Ser Asn Gly Pro His Trp
145                 150                 155                 160
Ala His Gln Arg Arg Ile Ile Ala Pro Glu Phe Phe Leu Asp Lys Val
                165                 170                 175
Lys Gly Met Val Gly Leu Val Val Glu Ser Ala Met Pro Met Leu Ser
            180                 185                 190
Lys Trp Glu Glu Met Met Lys Arg Glu Gly Glu Met Val Cys Asp Ile
        195                 200                 205
Ile Val Asp Glu Asp Leu Arg Ala Ala Ser Ala Asp Val Ile Ser Arg
210                 215                 220
Ala Cys Phe Gly Ser Ser Phe Ser Lys Gly Lys Glu Ile Phe Ser Lys
225                 230                 235                 240
Leu Arg Cys Leu Gln Lys Ala Ile Thr His Asn Asn Ile Leu Phe Ser
                245                 250                 255
Leu Asn Gly Phe Thr Asp Val Val Phe Gly Thr Lys Lys His Gly Asn
            260                 265                 270
Gly Lys Ile Asp Glu Leu Glu Arg His Ile Glu Ser Leu Ile Trp Glu
        275                 280                 285
Thr Val Lys Glu Arg Glu Arg Glu Cys Val Gly Asp His Lys Lys Asp
            290                 295                 300
Leu Met Gln Leu Ile Leu Glu Gly Ala Arg Ser Ser Cys Asp Gly Asn
305                 310                 315                 320
Leu Glu Asp Lys Thr Gln Ser Tyr Lys Ser Phe Val Val Asp Asn Cys
                325                 330                 335
Lys Ser Ile Tyr Phe Ala Gly His Glu Thr Ser Ala Val Ala Val Ser
            340                 345                 350
Trp Cys Leu Met Leu Leu Ala Leu Asn Pro Ser Trp Gln Thr Arg Ile
        355                 360                 365
Arg Asp Glu Val Phe Leu His Cys Lys Asn Gly Ile Pro Asp Ala Asp
370                 375                 380
Ser Ile Ser Asn Leu Lys Thr Val Thr Met Val Ile Gln Glu Thr Leu
385                 390                 395                 400
Arg Leu Tyr Pro Pro Ala Ala Phe Val Ser Arg Glu Ala Leu Glu Asp
                405                 410                 415
Thr Lys Leu Gly Asn Leu Val Val Pro Lys Gly Val Cys Ile Trp Thr
            420                 425                 430
Leu Ile Pro Thr Leu His Arg Asp Pro Glu Ile Trp Gly Ala Asp Ala
        435                 440                 445
Asn Glu Phe Asn Pro Glu Arg Phe Ser Glu Gly Val Ser Lys Ala Cys
            450                 455                 460
Lys His Pro Gln Ser Phe Val Pro Phe Gly Leu Gly Thr Arg Leu Cys
465                 470                 475                 480
```

```
Leu Gly Lys Asn Phe Gly Met Met Glu Leu Lys Val Leu Val Ser Leu
            485                 490                 495

Ile Val Ser Arg Phe Ser Phe Thr Leu Ser Pro Thr Tyr Gln His Ser
            500                 505                 510

Pro Val Phe Arg Met Leu Val Glu Pro Gln His Gly Val Val Ile Arg
            515                 520                 525

Val Leu Arg Gln
    530

<210> SEQ ID NO 7
<211> LENGTH: 24
<212> TYPE: DNA
<213> ORGANISM: artifitial sequence
<220> FEATURE:
<221> NAME/KEY: misc_feature
<223> OTHER INFORMATION: primer

<400> SEQUENCE: 7
tgaggatcca aataaaataa aaag                                          24

<210> SEQ ID NO 8
<211> LENGTH: 24
<212> TYPE: DNA
<213> ORGANISM: artifitial sequence
<220> FEATURE:
<221> NAME/KEY: misc_feature
<223> OTHER INFORMATION: primer

<400> SEQUENCE: 8
aaagtcgacc acacacaaag caaa                                          24

<210> SEQ ID NO 9
<211> LENGTH: 21
<212> TYPE: DNA
<213> ORGANISM: artificial sequence
<220> FEATURE:
<221> NAME/KEY: misc_feature
<223> OTHER INFORMATION: primer

<400> SEQUENCE: 9
ctgctgcaga ctctatttcc a                                             21

<210> SEQ ID NO 10
<211> LENGTH: 25
<212> TYPE: DNA
<213> ORGANISM: artificial sequence
<220> FEATURE:
<221> NAME/KEY: misc_feature
<223> OTHER INFORMATION: primer

<400> SEQUENCE: 10
ttcaggatcc tttacttttt atttt                                         25

<210> SEQ ID NO 11
<211> LENGTH: 20
<212> TYPE: DNA
<213> ORGANISM: artificial sequence
<220> FEATURE:
<221> NAME/KEY: misc_feature
<223> OTHER INFORMATION: primer

<400> SEQUENCE: 11
aatggtacca caagaaacaa                                               20

<210> SEQ ID NO 12
<211> LENGTH: 21
```

```
<212> TYPE: DNA
<213> ORGANISM: artificial sequence
<220> FEATURE:
<221> NAME/KEY: misc_feature
<223> OTHER INFORMATION: primer

<400> SEQUENCE: 12
tctagatttg agctgaaaaa a                                                  21

<210> SEQ ID NO 13
<211> LENGTH: 1491
<212> TYPE: DNA
<213> ORGANISM: Arabidopsis thaliana

<400> SEQUENCE: 13
ctgacgcaga ctctatttcc aacctcaaaa cggtaattta caagttacaa ccttgcctct        60
catgtcaagt tccttaaact ctcttaaacc aaaaaaaaaa atgttccttg gactccaagt       120
atgactattt tcataaccta acatcacttg aataaaaata taggtgacaa tggttatcca       180
ggaaacgttg aggctatacc caccagcagc attcgtgtcg agagaagccc ttgaggacac       240
aaaactcgga aacctcgtgg tgccaaaggg agtgtgcatc tggacgttga tccctacatt       300
gcacagagac cctgagatat ggggagctga cgcaaatgaa ttcaatccag aaagatttag       360
cgaaggagtc tctaaagcct gcaaacaccc tcagtcattc gtcccatttg cttagggac       420 aaggttgtgt ttaggaaaga attttggtat gatggagctc aaggttcttg tctcacttat       480
tgtgtcaagg tttagcttta ctctctctcc cacatatcaa cactctccgg tgtttagaat       540
gcttgtagag cctcaacatg gtgttgtcat tagagttctg agacaataag atatgtcgtt       600
agcttatggt tttagttta atcctgtgta ataataagat attattacac tatagtacta       660
taatagtatt ttctttggta tctttttttt tttgttctgt atatacagat ttaccaatag       720
tcatcgaaaa aaatcagttg tctactaaaa gtaactagct agcttgtaac ttattcattc       780
gaaaaagaaa ttaaaaaact attcgtaact agcatgttat taaaagccta taaaacaaat       840
cattaaaatt aacaaatcgt tgtagtttaa attactaacc ttaattttat tataatttat       900
gtataaatac actctactgt ctctacctac ttatttgata gggtgttttt ttttgtcttt       960 ccttaaaatat agttatggat cttgaatcta cttagatttg taatgctttt aatcatttt      1020 tacactatta gactattagt actagatatt tagagtaaat aacttggatt tgctaaaatc      1080
atgaatactg attgatgaat gtttgagatc tacattgttt ctaagaaaac cgagattatt      1140
ccatagcttt gtttaggtcg tgttaagttt tcaaatataa gtccaagaac aattggacag      1200
ccaaggtcgt gctaaaagta tgtgggcttt tcaagcgtaa actgaaccgg gagtcccagg      1260
attgttccct gctgtgtaat atatttaata tttaataaaa taataaatat ctgcattttt      1320
attgtttcgt tagtctaatt gaacttattt gttcaaagta gttatgattt aataaactaa      1380
aattttggac ttatttgttc aaaaggaatc tggttgacta taatatggtt caagaagtga      1440
agatgcaaat aaaataaaaa gtaaaagatc ctgaatagac aaaaagttaa a               1491
```

PLANT HEIGHT REGULATORY GENE AND USES THEREOF

FIELD OF THE INVENTION

The present invention relates to the fields of genetic technology and botany. In particular, the present invention relates to a plant height regulatory gene and uses thereof.

A "Sequence Listing" file, which was named "Sequence Listing.txt" and created on Feb. 4, 2010 and having 23.3 Kb in size, was filed electronically with this application. Pursuant to 37 C.F.R. §1.52(e)(5), the content of this file is incorporated by reference.

BACKGROUND OF THE INVENTION

Currently, the investigation for high-yield crop breeding mainly focuses on improving the plant type and panicle traits. Many high-yielding crop varieties have been developed to date due to the progression of cultivar improvement.

However, one major problem existing in many high-yield crops, such as high-yield rice cultivars (especially, super hybrid rice varieties), is over-height of the plants. The over-height can result in a higher tendency of lodging (beaten flat to ground) and limiting the potential for higher yields. This issue significantly impacts further increases in crop yields and wide adoption of the high-yield varieties.

Accordingly, it is necessary, in the art, to develop a method for regulating the heights of crop plants, in order to further improve the crop traits and increase the crop yields.

SUMMARY OF THE INVENTION

The object of the present invention is to provide a plant height regulatory gene and uses thereof.

In the first aspect, the invention provides isolated plant height regulatory polypeptides, selected from the group consisting of:

(a) a polypeptide having the amino acid sequence set forth in SEQ ID NO: 3; and (b) a polypeptide derived from (a), comprising substitution, deletion, or addition of one or more amino acid residues in the amino acid sequence set forth in SEQ ID NO:3 and having a plant height regulatory function.

In a preferred embodiment, said polypeptide is the polypeptide having the amino acid sequence set forth in SEQ ID NO: 3.

In a second aspect, the invention provides isolated polynucleotides each having a nucleotide sequence selected from the group consisting of:

(a) a polynucleotide encoding the polypeptide described above; and (b) a polynucleotide complementary to the polynucleotide of (a).

In a preferred embodiment, the polynucleotide encodes a polypeptide having the amino acid sequence set forth in SEQ ID NO:3.

In another preferred embodiment, the sequence of the polynucleotide has the nucleotide sequence set forth in SEQ ID NO: 2; or the nucleotide sequence set forth in SEQ ID NO: 1.

In a third aspect, the invention provides vectors each comprising a polynucleotide described above.

In a fourth aspect, the invention provides genetically engineered host cells each comprising a vector described above.

In a fifth aspect, the invention provides plants each comprising a polynucleotide described above.

In a sixth aspect, the invention provides methods for producing the plants described above, wherein a method comprises introducing a polynucleotide described above into a plant.

In a preferred embodiment, a method described above comprises:

(1) providing *Agrobacterium* cells carrying an expression vector containing a polynucleotide described above;

(2) contacting cells, tissues, or organs of a plant with the *Agrobacterium* cells described in the step (1), to introduce said polynucleotide into the plant cells, and allowing the polynucleotide to integrate into the chromosomes of the plant cells;

(3) selecting the plant cell, tissue, or organ containing said polynucleotide; and (4) allowing the plant cell, tissue, or organ described in the step (3) to regenerate a new plant.

In a seventh aspect, the invention provides methods for producing a plant. Each method comprises crossbreeding the plant with the introduced polynucleotide with a non-transgenic plant, thereby obtaining hybrid offspring containing said polynucleotide.

In an eighth aspect, the invention provides methods for producing a polypeptides described above. A method comprises:

(a) culturing a host cell containing said polynucleotide under a condition suitable for expression;

(b) isolating said polypeptide from the culture.

In a ninth aspect, the invention provides uses of a polypeptide or its encoding polynucleotide described above in:

regulating plant heights, volumes, tillerings, yields, flower organ sizes, or seed sizes of crops; or preparing a material for regulating plant heights, volumes, tillerings, yields, flower organ sizes, or seed sizes of crops.

In a tenth aspect, the invention provides methods for regulating plant heights, volumes, tillerings, yields, flower organ sizes, or seed sizes of crops. A method comprises regulating the expression or activity of a plant height regulatory gene in crops.

In another preferred embodiment, decreased plant heights and volumes, and increased tillerings and yields can be achieved by enhancement of the expression or activity of the plant height regulatory gene in crops; and increased flower organ sizes, seed sizes, plant heights, or volumes can be achieved by inhibition of the expression or activity of the plant height regulatory gene in crops;

In an eleventh aspect, the invention provides agonists or antagonists for a plant height regulatory polypeptide described above or its encoding gene.

In a twelfth aspect, the invention provides promoters for specific expression in plant stems or leaves. A promoter is selected from the group consisting of:

(1) a polynucleotide having the nucleotide sequence set forth in SEQ ID NO: 13;

(2) a polynucleotide capable of hybridizing to the polynucleotide sequence described in (1) under stringent conditions, and capable of directing specific expression of a target gene in plant stems or leaves; and (3) a polynucleotide having more than 70% (preferably more than 80%, more preferably more than 90%, most preferably more than 95%, such as 98%, 99%) identity with the nucleotide sequence set forth in SEQ ID NO:13 and capable of directing specific expression of a target gene in plant stems or leaves.

In the thirteenth aspect, the invention relates to uses of said promoters to direct specific expression of a target gene in plant stems or leaves.

In the fourteenth aspect, the invention provides constructs, each of which comprising a promoter described above for specific expression in plant stems or leaves.

In another preferred embodiment, a construct described above comprises at least one polyclonal site (such as restriction sites), for inserting a target gene, downstream of and operably linked to a promoter for specific expression in plant stems or leaves.

In another preferred embodiment, said construct is an expression vector.

In another preferred embodiment, said construct comprises the following elements operably linked to each other: said promoter and a target gene.

In another preferred embodiment, said target gene is an exogenous gene.

In another preferred embodiment, said target gene is a structural gene.

In another preferred embodiment, said target gene can encode a protein with a specific function.

In another preferred embodiment, said target gene is located less than 2000 bp (preferably less than 1000 bp, more preferably less than 500 bp, most preferably less than 300 bp) downstream of said promoter.

In light of the description provided herein, other aspects of the invention would be apparent to those skilled in the art.

SPECIFIC EMBODIMENTS

Figure 1:
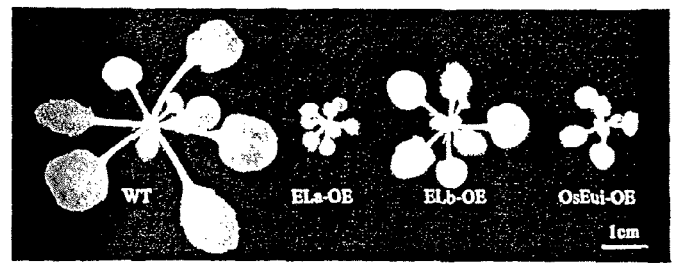
FIG. 1 shows a top view of a wild-type (Wt) *Arabidopsis* plant and an ELb (Eui-like b) over-expressing transgenic *Arabidopsis* (ELb-OE) plant. An ELa (Eui-like a) over-expressing transgenic *Arabidopsis* (ELa-OE) plant and a rice OsEui over-expressional transgenic *Arabidopsis* (OsEui-OE) plant act as controls.

By extensive researches, the inventors discovered an ELb gene useful for regulating plant heights, volumes, tillerings, yields, flower organ sizes, and seed sizes in crops. It is possible to decrease the plant heights and volumes and increase effective tillering numbers and yields of crops by increasing the expression of this gene. It is also possible to increase flower organ sizes and seed sizes by decreasing the expression of this gene. The present invention is based on these findings.

As used herein, the term "crop" or "crops" include, but are not limited to: *Gramineae, Cruciferae*, and xylophyta, and the like. More preferably, the *Gramineae* includes, but is not limited to: rice, wheat, barley, maize, sorghum, and the like; or the *Cruciferae* includes, but is not limited to: *Arabidopsis*.

As used herein, "isolated" refers to material isolated from its original environments (original environments are natural environments for natural material). For example, natural polynucleotides and polypeptides in living cells are non-isolated or non-purified, but polynucleotides and polypeptides are isolated or purified when separated from other materials which commonly accompany them in natural states.

As used herein, "an isolated plant height regulatory polypeptide," "an isolated ELb protein", or "an isolated ELb polypeptide" refers to an ELb protein substantially free from other proteins, lipids, saccharides, or other materials which accompany ELb protein in natural states. Those skilled in the art are capable of purifying ELb protein using standard protein purification techniques. A substantially pure polypeptide forms a single main band in a non-reduction polyacrylamide gel.

As used herein, the term "contain," "having," or "comprise" includes the meaning of "including," "mainly composed of," "substantially composed of," and "composed of"; "mainly composed of," "substantially composed of" and "composed of" are specific terms of "contain," "having," or "comprise."

ELb Polypeptide and Uses Thereof

Polypeptides of the invention can be recombinant polypeptides, natural polypeptides, or synthetic polypeptides, preferably recombinant polypeptides. Polypeptides of the invention can be purified natural products, or chemically synthesized products, or products derived from prokaryotic or eukaryotic hosts (such as bacterial, yeast, higher plant, insect, and mammalian cells) using recombinant techniques. Polypeptides of the invention can be glycosylated or non-glycosylated, depending on the host cells used for recombinant production. Polypeptides of the invention may or may not comprise a methionine residue at the initiating site.

The invention further includes fragments, derivatives, and analogues of ELb proteins. As used herein, the term "fragment", "derivative", and "analogue" refer to a polypeptide that retains substantially the same biological functions or activities as ELb polypeptides of the invention. The fragments, derivatives, and analogues of the invention can be (i) a polypeptides with one or more conservative or non-conservative amino acid residues (preferably conservative residue) substituted, said substituted residues may or may not be encoded by genetic codes, or (ii) a polypeptides with substituent group(s) in one or more amino acid residues, or (iii) a polypeptide derived from a mature polypeptide coupled to another compound (such as compound capable of extending the half life of a polypeptide, e.g. polyethylene glycol), or (iv) a polypeptide derived from said polypeptide coupled to an additional amino acid sequence (e.g. a leading sequence, a secretion sequence, a sequence used to purify said polypeptide, a proteinogen sequence, or a fusion protein). As defined herein, these fragments, derivatives, and analogues are well known to those skilled in the art.

In the invention, the term "ELb protein" means the polypeptide set forth in SEQ ID NO: 3 having the activity of ELb protein. This term also includes variants of the polypeptide of SEQ ID NO: 3 having the same function as ELb protein. These variants include (but are not limited to) deletion, insert, and/or substitution of several (generally 1-50, preferably 1-30, more preferably 1-20, most preferably 1-10, still more preferably 1-8 or 1-5) amino acids, as well as addition of one or more (generally less than 20, preferably less than 10, more preferably less than 5) amino acids to the C-terminal and/or N-terminal. For example, functions of proteins typically are not changed by substitution of one amino acid with another amino acid having the same or similar property. As another example, functions of proteins typically are not changed by addition of one or several amino acids to C-terminal and/or N-terminal as well. This term, ELb protein, also includes active fragments and derivatives of ELb protein.

The variants of a polypeptide include: homologous sequences, conservative variants, allelic variants, natural mutants, induced mutants, proteins encoded by a DNA sequence that hybrids to an ELb-protein encoding DNA sequence under high or low stringent conditions, and polypeptides or proteins obtained using antibodies against the ELb protein. The invention also provides other polypeptides, such as fused proteins comprising ELb protein or a fragment thereof. In addition to almost full-length polypeptide, the invention further comprises soluble fragments of ELb protein. These fragments generally comprise at least about 20 contiguous amino acids, typically at least about 30 contiguous amino acids, preferably at least about 50 contiguous amino acids, more preferably at least about 80 contiguous amino acids, most preferably at least about 100 contiguous amino acids in the sequence of ELb protein.

The invention further provides analogues of ELb proteins or polypeptides. The difference between these analogues and the native ELb protein could be the difference in amino acid sequence, the difference in modification patterns not resulting in any sequence change, or both. These polypeptides include natural or induced genetic variants. The induced variants can be obtained by various techniques, such as random mutagenesis by exposure to radiation or mutagen, as well as site-directed mutagenesis or other known molecular biology techniques. These analogues also include the analogues containing a residue (e.g. D-amino acid) different from the natural L-amino acid residues, and analogues containing a non-naturally occurring or synthetic amino acid (e.g. β, γ-amino acid). It should be understood that the polypeptides of the invention are not limited to the representative polypeptides described above.

The modified (generally not resulting in primary structure change) forms include: chemically derived form, such as acetylated or carboxylated form, of a peptide in vivo or in vitro. The modifications also include glycosylation. The modified forms also include a sequence containing a phosphorylated amino acid (e.g. phosphotyrosine, phosphoserine, phosphothreonine), or a polypeptide modified to enhance resistance to proteolysis or optimize solubility.

In the present invention, "a conservative variant polypeptide of ELb protein" refers to the polypeptides containing up to 20, preferably at most 10, more preferably at most 5, most preferably at most 3 amino acids substituted by other amino acids with similar or comparable properties in comparison with the amino acid sequence set forth in SEQ ID NO:3. Preferably, these conservative variant peptides are produced by substitution of amino acids according to table 1.

TABLE 1

| Amino acid residue | Representative substitution | Preferred substitution |
| --- | --- | --- |
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |

TABLE 1-continued

| Amino acid residue | Representative substitution | Preferred substitution |
| --- | --- | --- |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

The invention further provides polynucleotide sequences encoding the ELb proteins of the invention or conservative variant polypeptides thereof.

Polynucleotides of the invention can be DNA or RNA. DNA includes cDNA, genomic DNA, or artificial synthetic DNA. DNA can be single-stranded or double-stranded. DNA can be a coding strand or a non-coding strand. The coding region sequence encoding a mature polypeptide can be the same as the coding region sequence set forth in SEQ ID NO: 2 or a degenerate variant thereof. As used herein, "degenerate variant" means a polynucleotide sequence encoding a protein with the sequence set forth in SEQ ID NO: 3, but differing from the coding the region sequence set forth in SEQ ID NO:2.

Polynucleotides encoding a mature polypeptide set forth in SEQ ID NO:3 include: a coding sequence only encoding a mature polypeptide; a sequence encoding a mature polypeptide and various additional coding sequences; a sequence encoding a mature polypeptide (and any additional coding sequence) and non-coding sequence.

The term "a polynucleotide encoding a polypeptide" refers to a polynucleotide encoding the polypeptide, or a polynucleotide further containing additional coding and/or non-coding sequences.

The invention also relates to variants of the above polynucleotides, encoding polypeptides with the same amino acid sequences as described herein or fragments, analogues, and derivatives thereof. The variants of the polynucleotides can be naturally occurring allelic variants or non-naturally occurring variants. These nucleotide variants include substitution variants, deletion variants, and insertion variants. As known in the art, an allelic variant is an alternative of a polynucleotide, which can include one or more substituted, deleted, or inserted nucleotides, which do not result in substantial function changes in the polypeptide encoded by the variant.

The invention also relates to polynucleotides which hybrid to the sequences described above and having at least 50%, preferably at least 70%, more preferably at least 80% identity with the sequences described above. The invention particularly relates to polynucleotides hybridizing to the polynucleotides described herein under stringent conditions. In the invention, "stringent conditions" refer to (1) hybridization and wash under lower ionic strength and higher temperature, such as 0.2×SSC, 0.1% SDS, 60° C.; or (2) hybridization in the presence of a denaturant, such as 50% (v/v) formamide, 0.1% bovine serum/0.1% Ficoll, 42° C., etc; or (3) hybridization occurring only between two sequences having at least 80%, preferably at least 90%, more preferably more than 95% identity. Moreover, the biological functions and activities of polypeptides encoded by the hybridizable polynucleotides are the same as those of the mature polypeptide set forth in SEQ ID NO:3.

The invention also relates to polynucleotide fragments hybridizing to the sequences described above. As used herein, a "polynucleotide fragment" comprises at least 15, preferably at least 30, more preferably at least 50, most preferably at least 100 or more nucleotides in length. The polynucleotide fragments can be used with nucleic acid amplification techniques (e.g. PCR) to determine and/or isolate polynucleotides encoding ELb protein.

It should be understood that in accordance with embodiments of the invention, ELb gene is preferably derived from *Arabidopsis*. However, embodiments of the invention also include other genes which have high homology (for example, more than 60%, such as 70%, 80%, 85%, 90%, 95%, even 98% sequence identity) with the *Arabidopsis* ELb gene and are derived from other plants. The alignment methods and means for determining sequence identity or homology (such as BLAST) are well known in the art.

The full length nucleotide sequences encoding ELb protein of the invention, or fragments thereof can be produced using PCR amplification, recombinant technology, or chemical synthesis. For PCR amplification, the primers can be designed according to the related nucleotide sequences, especially the sequences of open reading frames, disclosed, and commercially available cDNA library or cDNA library made by routine methods known to those skilled in the art can be used as templates. Using these primers and libraries, PCR amplification can be carried out to obtain the desired sequences. When the sequences are long, it is usually necessary to perform PCR twice or multiple times, and then ligate the amplified fragments in a correct order.

Once a desired sequence is obtained, a large amount of the desired sequence can be obtained by recombinant techniques. Usually, the desired sequence is cloned into a vector, and the vector is introduced into cells, and then the desired sequences are isolated from propagated host cells by routine methods.

In addition, the desired sequences, especially shorter fragments can be produced by chemical synthesis. In general, multiple small fragments may be first synthesized, and then ligated together to produce a long fragment.

Currently, it is possible to obtain a DNA sequence encoding a protein of the present invention (or fragment or derivative thereof) exclusively by chemical synthesis. Then, this DNA can be introduced into various existing DNA molecules (e.g. vectors) and cells known in the art. In addition, some mutations can be introduced into a protein of the present invention by chemical synthesis as well.

The invention also relates to vectors containing polynucleotides of the invention, host cells resulted from genetic engineering using these vectors or ELb protein-encoding sequences, as well as methods for preparing polypeptides of the invention by recombinant techniques.

Using conventional DNA recombinant techniques (Science, 1984; 224:1431), polynucleotide sequences of the invention can be used to express or produce recombinant ELb proteins. This typically comprises the following steps:

(1) transforming or transducing suitable host cells with a polynucleotide (or its variants) encoding ELb protein, or a recombinant expression vector containing said polynucleotide;

(2) culturing the host cells in an appropriate medium;

(3) isolating and purifying the protein from the medium or cells.

In the invention, the polynucleotide sequence encoding ELb protein can be inserted into a recombinant expression vector. The term "recombinant expression vector" means bacterial plasmid, phage, yeast plasmid, plant cell virus, mammalian cell virus, or other vectors. Altogether, any plasmid and vector can be used provided that they are capable of replicating and stabilizing in the host. An important feature of the expression vector is having a replication origin, a promoter, a maker gene, and a translation control element.

An expression vector containing an ELb protein-encoding DNA sequence and appropriate transcription/translation control signals can be constructed using methods well known to those skilled in the art. These methods include in vitro recombinant DNA techniques, DNA synthesis techniques, in vivo recombinant techniques, and the like. Said DNA sequence can be effectively linked to an appropriate promoter in the expression vector in order to direct mRNA synthesis. An expression vector may also comprise a ribosome binding site as a translation initiation site and a transcription terminator.

In addition, an expression vector preferably comprises one or more selectable marker genes, such as dihydrofolate reductase, neomycin resistance, or green fluorescent protein (GFP) useful in eukaryotic cell culture, or kanamycin resistance or ampicillin resistance useful in *E. coli* culture, to provide phenotypes useful in selecting the transformed host cells.

A vector containing an appropriate DNA sequence described above and an appropriate promoter or control sequence described above can be used to transform suitable host cells for expression of the proteins.

The host cells can be prokaryotic cells, such as bacterial cells; or lower eukaryotic cells, such as yeast cells; or higher eukaryotic cells, such as plant cells. Representative examples are *E. coli, Streptomyces, Agrobacterium*; fungal cells, e.g., yeast; plant cells, and the like.

An inserted enhancer sequence in a vector will enhance transcription when a polynucleotide of the invention is expressed in higher eukaryotic cells. An enhancer, a DNA cis-acting factor, generally comprises about 10-300 base pairs, and acts on the promoter to enhance gene transcription.

Those having ordinary skill in the art would understand how to select appropriate vectors, promoters, enhancers, and host cells.

Transformation of host cells with recombinant DNA can be carried out using routine techniques well known to one skilled in the art. For prokaryotic hosts, such as *E. coli*, the competent cells capable of absorbing DNA can be obtained by harvesting cells after exponential growth phase and treating the cells with $CaCl_2$. These preparation methods are well known in the art. Another method uses $MgCl_2$ treatment. Transformation can also be carried out by electroporation, if necessary. For eukaryotic hosts, one can use any suitable DNA transfection methods, e.g. calcium phosphate coprecipitation, routine mechanical methods such as microinjection, electroporation, liposome-encapsulation, and the like. The plant cells can be transformed using methods like *Agrobacterium* transformation or gene gun transformation, and other techniques such as leaf dish method, transformation of immature rice embryo, and so on. The transformed plant cells, tissues, or organs are allowed to regenerate new plants by conventional methods, to obtain plants with changed traits.

The resulting transformants can be grown routinely to express the polypeptide encoded by the genes of the invention. The culture medium can be selected from various conventional media, depending on the host cells used. The culture is performed under conditions suitable for host cell growth. The selected promoter may be induced using an appropriate method (e.g. temperature changes or chemical inducements) when host cells are grown to an appropriate density, and then the cells are cultured for an additional period.

The recombinant polypeptides described above can be expressed intracellularly or on cell membrane, or secreted by cells. If necessary, the recombinant proteins can be isolated and purified by various isolation methods taking advantage of their physical, chemical, and other properties. These methods are well known to those skilled in the art. The examples of such methods include, without limitation, conventional renaturation treatments, treatments with protein precipitant (salting out), centrifuge, breaking bacteria by osmosis, ultratreatment, ultracentrifugation, molecular sieve chromatography (gel filtration), adsorption chromatography, ion exchange chromatography, high-performance liquid chromatography (HPLC), and other liquid chromatography, and combination thereof.

The recombinant ELb proteins can be used to, for example, screen for antibodies, polypeptides, or other ligands capable of enhancing or inhibiting ELb protein functions. Screening a polypeptide library with expressed recombinant ELb protein can be used to search for valuable polypeptide molecules that inhibit or stimulate ELb protein functions.

A portion or the whole polynucleotides of the invention can be immobilized on a microarray or DNA chip ("gene chip") as probes for analysis of differential gene expression in the tissues. The transcripts of ELb protein can be detected by in vitro amplification using RNA-polymerase chain reaction (RT-PCR) and specific primers for ELb protein.

The invention also relates to methods for crop improvement, comprising regulation of the expression or activity of ELb gene or a homologous gene thereof in the plants. Whether enhancing or inhibiting ELb expression or activity would depend on the plant traits to be improved. The need for decreased plant heights and volumes, or increased plant tillering and yields can be met by increasing ELb expression or activity in crops; alternatively, the need for increased flower organ sizes, seed sizes, plant heights, or volumes can be met by inhibiting the expression or activity of plant height regulatory genes in crops.

Methods for increasing expression of ELb gene or a homologous gene thereof are well known in the art. For example, an expression construct containing an ELb-encoding gene may be introduced into a plant to overexpress ELb; or enhancement of expression of ELb gene or a homologous gene thereof can be driven by a strong promoter; or the expression of ELb gene can be enhanced by an enhancer (e.g. the first intron of rice waxy gene, the first intron of Actin gene, etc.). Strong promotors suitable for these methods include, but are not limited to: 35S promoter, Ubi promoters of rice and maize, etc.

Methods for inhibition of expression of ELb gene or a homologous gene thereof are well known in the art. For example, inhibition can be accomplished by RNA interference (RNAi) or gene silencing (knock-out) techniques.

As a preferable embodiment of the invention, a method for obtaining a plant with high expression of ELb comprises the following steps:

(1) providing *Agrobacterium* cells carrying an expression vector containing DNA coding sequence of ELb protein;

(2) contacting cells, tissues, or organs of the plant with the *Agrobacterium* cells described in step (1), to introduce said DNA coding sequence of ELb protein into the plant cells, tissues or organs and allow them to integrate into the chromosomes of the plant cells;

(3) selecting the plant cells, tissues or organs containing said DNA coding sequence of ELb protein; and (4) allowing the plant cells, tissues or organs described in step (3) to regenerate a new plant.

Any appropriate routine means, including reagent, temperature, pressure, etc. can be used to practice this method.

The present invention further relates to agonists or antagonists of ELb protein or coding gene thereof. The agonists or antagonists can regulate ELb activity or expression, therefore can be used to regulate plant heights, volumes, tillerings, yields, flower organ sizes, or seed sizes, and the like, in crops by their effects on ELb functions, in order to achieve the goal for traits improvement.

An ELb antagonist refers to an agent capable of decreasing ELb activity and stability, down-regulating ELb expression, decreasing ELb effective acting time, or inhibiting ELb transcription or translation. These agents can be used, according to the present invention, as useful agents for increasing flower organ sizes, seed sizes, plant heights, or volumes of crops.

An ELb agonist refers to an agent capable of increasing ELb activity, maintaining ELb stability, promoting ELb expression, increasing ELb effective acting time, or promoting ELb transcription or translation. These agents can be used, in accordance with the present invention, as useful agents for decreasing plant heights and volumes, and increasing tillerings and yields of crops.

In one embodiment, the invention relates to an ELb gene having a genomic sequence as set forth in SEQ ID NO:1, wherein the open reading frame (ORF) is located in regions 61-353, 1363-1585, 1690-1943, 2028-2414, 2559-2979, and the full length cDNA (SEQ ID NO:1) has 1578 bp encoding a protein comprising 525 amino acids (SEQ ID NO:3). The ELb gene provides a new means for improvement of plant heights, volumes, yields, tillerings, and etc. of crops, and has therefore a promising prospect.

The Promoter for Specific Expression in Plant Stems or Leaves, and Directing Gene Expression As used herein, the "promoter" or "promoter region" means a nucleotide sequence usually located upstream (5') of the coding sequence of a target gene, which initiates polynucleotide sequence transcription into mRNA. In general, a promoter or promoter region can provide a recognition site for RNA polymerases and other factors necessary for correct initiation of transcription. Herein, the promoter or promoter region includes a promoter variant, i.e., a naturally occurring allelic variant or a non-naturally occurring variant, including a substitution variant, a deletion variant, and an insertion variant.

As used herein, "tissue-specific promoter" or "organ-specific promoter" means that gene expression usually occurs only in certain specified organs or tissues under the control of these promoters.

As used herein, "operably linked" means the functional spatial arrangement of two or more nucleic acid regions or nucleic acid sequences. For example, a promoter region is located in at specified position relative to the nucleic acid sequence of a target gene, so that the transcription of the nucleic acid sequence is under control of the promoter region, accordingly, the promoter region can be "operably linked" to the nucleic acid sequence.

Generally, a promoter is considered tissue-specific or organ-specific if the mRNA expression in a tissue or organ is at least 2 times, preferably at least 5 times, more preferably at least 10 times, more preferably at least 25 times, more preferably at least 50 times, still more preferably at least 100 times, most preferably at least 1000 times higher than in other tissues or organs.

The invention relates to a promoter selected from the group consisting of:

(1) a polynucleotide having nucleotide sequence set forth in SEQ ID NO:13; or (2) a polynucleotide hybridizing to the polynucleotide sequence described in (1) under a stringent condition and directing specific expression of a target gene in plant stems or leaves.

In the invention, a "stringent condition" refers to (1) hybridization and wash under lower ionic strength and higher temperature, such as 0.2×SSC, 0.1% SDS, and 60° C.; or (2) hybridization in the presence of a denaturant, such as 50% (v/v) formamide, 0.1% bovine serum/0.1% Ficoll, and 42° C., etc; or (3) hybridization occurring only between two sequences having at least 80%, preferably at least 90%, more preferably more than 95% identity. Moreover, the hybridizable polynucleotide can direct specific expression of a target gene in plant stems or leaves.

Polynucleotide hybridization is a technique well known to those skilled in the art, and hybridization profile for a pair of specified polynucleotides indicates their similarity or identity. Therefore, the invention further relates to a polynucleotide hybridizing to the nucleotide sequence set forth in SEQ ID NO: 13 and having at least 50%, preferably at least 60%, more preferably at least 70%, still more preferably at least 80%, even still more preferably at least 85%, more preferably at least 90% (e.g., 95%, 96%, 97%, 98%, or 99%) identity with the nucleotide sequence set forth in SEQ ID NO: 13.

A promoter of the invention is specific for plant tissue or organ, in particular, for plant stems or leaves. In some embodiments of the invention, the inventors have discovered that ELb gene or GUS gene can be specifically expressed in plant stems and leaves, but substantially not expressed in other tissues or organs, under the control of a promoter of the invention.

A promoter of the invention can be operably linked to a target gene which can be exogenous (heterogenous) to the promoter. The target gene is usually an nucleotide sequence (preferably a structural nucleotide sequence), and preferably encodes a protein with a specified function, such as certain proteins regulating growth of plant stems and leaves, in particular, the proteins associated with plant heights, in accordance with embodiments of the invention.

A promoter of the invention can also be operably linked to an improved target gene which is exogenous (heterogenous) to the promoter. The target gene may be improved to have various desirable properties, such as enhanced expression, altered post-translational modification (e.g. phosphorylation site), transport of translation product out of the cell, improved stability, insertion or deletion of a cellular signal, and so on.

In addition, the promoter and target gene can be designed to down-regulate a specified gene, which is usually achieved by linking the promoter to the target gene sequence, and initiating the sequence in a reverse direction and in an antisense manner. Those skilled in the art are familiar with the antisense techniques. Any nucleotide sequences can be regulated in this way.

Any promoter and target gene sequence described above can be included in a construct, in particular, a recombinant vector.

A recombinant vector usually comprises an operably linked (generally 5'→3') promoter for initiating transcription of a target gene and the target gene. If necessary, a recombinant vector can further comprise a 3' transcription terminator, a 3' polyadenylation signal, other non-translational nucleotide sequences, a transporting or targeting nucleotide sequence, a resistance selection marker, an enhancer, or an operon.

In general, a target gene is located less than 2000 bp (preferably less than 1000 bp, more preferably less than 500 bp, most preferably less than 300 bp) downstream of the promoter for specific expression in plant stems or leaves.

In addition to a promoter of the invention, the recombinant vector can further comprise one or more other promoters, such as tissue-specific, constitutive, or inducible promoters.

A vector containing an appropriate promoter described above and a target gene can be used to transform suitable host cells for protein expression.

The advantages of the invention are:

(1). providing a new isolated plant height regulatory gene which is capable of regulating plant heights, volumes, tillerings, yields, flower organ sizes, or seed sizes of crops; therefore, they can be used to improve crop cultivars.

(2). a regulatory gene of the invention may be transformed into crops to decrease plant heights, which can be useful in breeding for dwarf plant types, because moderately decreased plant heights and increased effective tillering numbers are ideotypes of high-yield breeding. For example, different expression levels in *Gramineae* crops could be used to decrease the plant heights to different extents to increase effective tillering numbers and yields.

(3) a promoter of the plant height regulatory gene is isolated for the first time, which directs specifically expression in plant stems or leaves, and can be used to regulate specific expression of a target gene in plant stems or leaves.

The invention is now further described in more detail in combination of the following examples. It should be understood that these examples are provided only for illustration without limiting the scope of the invention. The assays which are not particularly described in the following examples can be performed according to conventional procedures, as described in Sambrook et al, Molecular Cloning: Laboratory Manual (Cold Spring Harbor Laboratory Press, New York, 2001) or PCR primer: Laboratory Manual (Carl W. Dieffenbach and Gabriela S. Devksler eds., Cold Spring Harbor Laboratory Press, 1995), or as recommend by the manufacturers.

Materials 1.1 Plant Materials

*Arabidopsis thaliana*, the ecotype is Columbia (Col-0).

T-DNA inserted mutant: ELa (SALK_016089)

Rice cultiva: Taipei 309 (*Oryza sativa* L. ssp Japonica. cv Taipei309, TP309).

1.2 Bacterium Strains and Plasmid Vectors

*Agrobacterium tumefaciens*: GV3101 (see, Narasimhulu, S. B, et al, Gelvin. 1996. Early transcription of *Agrobacterium* t-DNA genes in tobacco and maize. Plant Cell 8:873-886), EHA105 (see, Hood, E. E. et al, 1993, New *Agrobacterium* helper plasmids for gene transfer to plants. Transgen. Res. 2:208-218).

Plasmid vectors:

pBluescript SK (pSK): purchased from Invitrogen Inc.

pCambia1300S: pCambia1300RS, purchased from CAMBIA.

pBI101.1: purchased from Invitrogen Inc.

pGEM-T Easy vector: purchased from Promega Inc.

RNAi vector 1300RS: available from Arkansas State University, USA.

1.3 Reagents and Enzymes

T4 DNA ligase, various restrictive endonucleases, and Taq DNA polymerase are purchased from MBI Ferment, TaKaRa, New England Biolabs, or Promega. A Recovery kit for DNA fragment in gel was purchased from Omega Inc. The Reverse Transcription System was purchased from GIBCOBRL. The molecular weight markers of nucleic acids are MBI products. The pGEM-Teasy vector was purchased from Promega Inc. (Madison, USA). The ($\alpha$-$^{32}$P) dCTP was purchased from YaHui Bioengineering Inc. (Beijing, China). A reverse transcription kit using SuperScript First-Strand Synthesis System for RT-PCR (#11904-018, Invitrogen) was used. Other conventional chemical reagents are analytically pure products imported or made in China. Various deoxynucleotide primers were synthesized by Sangon Inc, Shanghai, China. DNA sequences were determined by JiKang Inc., Shanghai; or Invitrogen Inc., Shanghai. Sequence analysis was completed using Genedoc, DNAStar software, and etc.

Methods

1. *Arabidopsis thaliana* Cultivation and Transformation

For sterile cultivation of *Arabidopsis thaliana*, the seeds were superficially (by 70% ethanol for 30 sec, then washed 4× with sterile water) and internally (by 7% sodium hypochlorite for 10 min, then washed 3× with sterile water) sterilized, and then sowed on ½ MS (½ Murashige and Skoog basal medium, 0.8% agar, pH 5.8) solid medium, placed at 4° C. for 72 hr, and subsequently transferred to 22° C. One week later, the seedlings were transplanted in artificial soil (vermiculite: black soil: pearlite=3:1:0.5) soaked by nutrient solution (HuaWuQue 3 g/10 L, YongTong Chemical Ltd, Shanghai, China), and subsequently transferred to an artificial climatic chamber with a diurnal cycle of 14/10 (L/D).

For *Arabidopsis thaliana* transformation, the plants aged 4-5 weeks in a favorable growth status (cutting off main scape 1 week before transformation, to promote developing more lateral scapes and more flowers, thereby increasing the transformation efficiency) were treated by sprinkle. The *Agrobacterium tumefaciens* cells containing the transgenic vectors were grown to $OD_{600}$ ~2.0 at 28° C., and then centrifuged at 4,000 rpm for 10 min, the pellet were resuspended in freshly prepared transformation solution (½ MS liquid medium containing 5% sucrose and 0.02% Silwet L-77), and grown to a final concentration as $OD_{600}$~0.6-0.8. The pollinated flowers and fruits were removed before transformation, and then the soil was allowed to absorb sufficient water. During transformation, the suspension of bacteria was sprinkled on the *Arabidopsis thaliana* plants until a few drops of the suspension dropped off from the leaves. The plants were covered by black bags to maintain humidity overnight in the dark. 24 hr later, the plants were transferred to normal conditions. 7 days later, the transformation was repeated once according to the procedure described above. The plants were collected and mixed in a paper bag after the seeds became mature. The collected plants were placed in a dessicator for 7 days, and then threshed. The sterilized seeds of T1 generation were sowed on ½×MS medium containing 50 μg/ml Kan or hygromycin, placed at 4° C. for 72 hr, and then placed under normal light condition.

2. The Gene Transformation of Callus of Mature Rice Embryo Mediated by *Agrobacterium tumefaciens*

(1) inducing callus of mature rice embryo

The seeds of rice 307T were hulled, then soaked with 70% ethanol for 1 min, and with 20% (v/v) sodium hypochlorite for 20-30 min, with continuous shaking. The seeds were rinsed with sterile water for 5-6 times. After suck-dried by sterile filter paper, the rice seeds were sowed on MSD medium and grown at 26° C. in the dark to induce callus. One week later, the endosperm, plumule, and radicle were removed to obtain callus, and the resulted callus were passaged on MSD in the dark. They were passaged every 2-3 weeks. For the callus of TP309 seeds, the medium used was NBD.

(2) Preparing the Bacteria Suspension Useful for Transformation

In morning of day 1: a small part of the bacteria stored at −70° C. was inoculated in 5 ml YEB (Rif 20 mg/L+Kan 50 mg/L) liquid medium, and cultured with shaking at 28° C. overnight.

In morning of day 2: 1-2 ml of YEB medium containing the bacteria were collected and transferred into 25-50 ml AB (20 mg/L Rif+50 mg/L Kan) liquid medium, and then grown at 28° C. for about 4 hr until $OD_{600}$~0.5.

(3) Co-culture

In the afternoon of day 2: after detection of $OD_{600}$ value, the bacteria suspension was centrifuged at 5,000 rpm for 15 min, the pellet was resuspended in AAM (containing AS100) and cultured until $OD_{600}$=0.4-0.6. The bacteria suspension was poured into a triangular flask containing rice callus, and the callus was soaked for 20 min with occasional shaking; after the bacteria suspension was suck-dried by sterile filter paper (or a pipette), the soaked callus were transferred on NBD (AS100) medium containing 2.5% Phytagel with a layer of sterile filter paper thereon, and were co-cultured for 2-3 days, and then, to each dish 1 ml AAM (+AS100) medium was added to sufficiently moisten the sterile filter paper.

(4) Screening

After suck-dried by sterile filter paper (another filter paper), the callus were transferred on screening medium containing hygromycin (Hyg) to screen resistant callus. The callus was cultured in dark for about 30 days, during which the screening medium was exchanged once.

The screening media used are:

the medium for the first screening containing 0.26% Phytagel MS+Timentin 100 mg/L+Hyg 30 mg/L;

the medium for the second screening containing 0.26% Phytagel NBD+Timentin 100 mg/L+Hyg 50 mg/L;

the medium for the third screening containing 0.26% Phytagel MS+Timentin 100 mg/L+Hyg 50 mg/L.

(5) Predifferentiation

The screened rice callus was transferred to a predifferentiation medium and grown for 10 days.

Predifferentiation medium: containing 0.45% Phytagel MS+BAP 2 mg/L+NAA 1 mg/L+ABA 5 mg/L Hyg 50 mg/L, pH 5.7, without 2,4-dichlorophenoxyacetic acid (2,4-D).

(6) Differentiation

The predifferentiated rice callus was transferred to a differentiation medium and cultivated to differentiate into a young plant (light, 15-30 days).

Differentiation medium: containing 0.45% Phytagel NB+BAP 3 mg/L+NAA 0.5 mg/L, pH 5.7, without 2,4-D.

(7) Rooting

The green young plant was transferred to a rooting medium for rooting.

Rooting medium: containing 0.45% Phytagel ½ MS+Hyg 50 mg/L, pH 5.7, without 2,4-D.

3. Vector Construction p35S::ELb Vector Construction cDNA coding region sequence of ELb protein was amplified by RT-PCR. The steps are as follows: total RNA of *Arabidopsis thaliana* plant was extracted by RNeasy Plant Mini kit (Qiagen) according to the instruction provided by the manufacturer, and then the resulted total RNA was reverse transcribed to produce ELb cDNA with M-MLV reverse transcriptase (Promega). The cDNA coding region sequence of ELb protein was amplified by a PCR reaction using Takara perobest DNA polymerase and the above cDNA used as templates. The primers used are:

```
Upstream primer (SEQ ID NO: 7):
5'-TGAGGATCCAAATAAAATAAAAAG-3'
(underlined: BamHI site);

Downstream primer (SEQ ID NO: 8):
5'-AAAGTCGACCACACACAAAGCAAA-3'
(underlined: ClaI site).
```

PCR condition: 94° C. for 3 min; 35 cycles of 94° C. for 30 sec, 58° C. for 30 sec, and 72° C. for 2 min; 72° C. for 10 min. The product was stored at 16° C.

PCR product was recovered and digested by both BamH1 and ClaI. The product was recovered, and then ligated to pSK vector which had also been digested and recovered as supra. The resulted vector was used to transform DH5α cells. The correct clone confirmed by restriction cleavage was selected for sequencing. For the clone with correct sequence confirmed by sequencing, the ELb cDNA coding region was cleaved by BamHI/ClaI and ligated into a double expression vector pCambia1300S cleaved by BamHI/ClaI, and transformed into DH5α cells to obtain transgenic clones. After extraction, the correct plasmid confirmed by restriction cleavage was transformed into *Agrobacterium tumefaciens* GV3101 and EHA105 cells. The plasmid was extracted from the *Agrobacterium tumefaciens* cells and re-transformed into DH5α cells. The plasmid was extracted from DH5α and cleaved by the restriction enzymes to verify the *Agrobacterium tumefaciens* cells transformed with the correct plasmid. The transgenic *Arabidopsis thaliana* plants were obtained by transformation of the *Arabidopsis thaliana* cells by sprinkle method, and the transgenic rice plants were obtained by *Agrobacterium tumefaciens* mediated genetic transformation of callus of mature rice embryo.

pELb Promoter::GUS Vector Construction

The upstream and downstream primers were designed based on the sequences (GeneID: 832559) available from GenBank, and the primers were within the range of 1.4 kb upstream of the translation initiation site of ELb gene. The genomic DNA extracted from a young plant (aged 7 days) of wild-typed *Arabidopsis thaliana* Columbia was used as template to perform PCR. Said primers are as follows:

```
Upstream primer (SEQ ID NO: 9):
5'-CTGCTGCAGACTCTATTTCCA-3'
(underlined: PstI site);

Downstream primer (SEQ ID NO: 10):
5'-TTCAGGATCCTTTACTTTTTATTTT-3'
(underlined: BamHI site);
```

Amplification condition: 94° C. for 3 min; 35 cycles of 94° C. for 30 sec, 58° C. for 30 sec, 72° C. for 2 min; 72° C. for 10 min. The product was stored at 16° C.

PCR product was cleaved by PstI/BamHI enzymes, and then ligated into the corresponding PstI/BamHI site in a pSK vector. The correct clone confirmed by restriction cleavage was selected for sequencing. For the clone with correct sequence confirmed by sequencing, the ELb promoter region (as set forth in SEQ ID NO:13) was cleaved by PstI/BamHI and ligated to a double expression vector pBI101.1 cleaved by PstI/BamHI, and transformed into *E. coli.* DH5α cells. After extraction, the correct plasmid confirmed by restriction cleavage was transformed into *Agrobacterium tumefaciens* GV3101 cells. The plasmid was extracted from the *Agrobacterium tumefaciens* cells and re-transformed into DH5α cells. The plasmid was extracted from DH5α and cleaved by the restriction enzymes to verify the *Agrobacterium tumefaciens* cells transformed with the correct plasmid. Meanwhile, the pBI101.1 vectors were transformed into GV3101 cells as negative and positive controls, respectively.

ELb Transgenic RNAi Plant Construction Under Background of ELa T-DNA Insertion Mutant The transgenic clone was constructed using RNAi vector 1300RS as follows: The genomic DNA of a young plant (aged 7 days) of wild-typed *Arabidopsis thaliana* Columbia was used as template to perform PCR to amplify a sequence of about 500 bp in the fourth exon of ELb gene. Said primers are as following:

```
Upstream primer (SEQ ID NO: 11):
5'-AATGGTACCACAAGAAACAA-3'
(underlined: KpnI site);

Downstream primer (SEQ ID NO: 12):
5'-TCTAGATTTGAGCTGAAAAAA-3'
(underlined: XbaI site).
```

Amplification condition: 94° C. for 3 min; 35 cycles of 94° C. for 30 sec, 50° C. for 30 sec, 72° C. for 30 sec; 72° C. for 10 min. The product was stored at 16° C.

PCR product was cleaved by KpnI/XbaI enzymes, and then ligated into the corresponding KpnI/XbaI site of pSK vector. The correct clone confirmed by restriction cleavage was selected for sequencing. For the clone with correct sequence confirmed by sequencing, the ELb partial fragment was cleaved by KpnI/XbaI and ligated to a double expression vector 1300RS cleaved by KpnI/XbaI, and transformed into *E. coli.* DH5α cells. After extraction, the correct plasmid confirmed by restriction cleavage was transformed into *Agrobacterium tumefaciens* GV3101 cells. The plasmid was extracted from the *Agrobacterium tumefaciens* cells and re-transformed into DH5α cells. The plasmid was extracted from DH5α and cleaved by the restriction enzymes to verify the *Agrobacterium tumefaciens* cells transformed with the correct plasmid.

The ELa T-DNA insertion mutant was transformed by sprinkle method to obtain the ELb RNAi transgenic plant (ELb RNAi/eLa) of *Arabidopsis thaliana* under the background of ELa T-DNA insertion mutant.

EXAMPLE 1

Cloning of ELb Gene

The inventor discovered 2 p450 monooxyganase genes, i.e., 714A1 and 714A2 bp searching the genomic sequences of *Arabidopsis thaliana* and performing bioinformatic research. They were initially predicted to involve in plant growth and development under the control of gibberellin, and designated as ELa (or AtEuila) and ELb (or AtEuilb) by the inventor.

The genomic DNA sequence of ELb gene coding region was set forth in SEQ ID NO:1; the cDNA sequence of ELb gene encoding region was set forth in SEQ ID NO:2; the ELb protein sequence was set forth in SEQ ID NO:3. The genomic sequence of ELa gene coding region was set forth in SEQ ID NO:4; the cDNA sequence of ELa gene coding region was set forth in SEQ ID NO:5; the ELa protein sequence was set forth in SEQ ID NO:6.

EXAMPLE 2

Decreased Plant Height and Volume in the Transgenic *Arabidopsis thaliana* Plants Overexpressing ELb Gene In this example, the inventor prepared transgenic *Arabidopsis thaliana* plants that overexpressed ELb, ELa, or OsEui, respectively. The wild-type (WT) plant, a transgenic plant overexpressing *Arabidopsis* ELa (ELa-OE), and a transgenic plant overexpressing rice OsEui were used as controls.

The growth profiles were observed after 4 weeks of growth, and the results are shown in FIG. 1. As shown in the figure, the wild type *Arabidopsis thaliana* plant was the largest, the ELb over-expressing plant were substantially smaller than the wild type plant, and the ELa over-expressing plant and the OsEui overexpressing plant were the smallest.

After 7 weeks of growth, the inventor determined the plant height of wild type plant, and plants overexpressing ELb, ELa, and rice OsEui, and the average plant height values were 26.2 cm, 14.2 cm, 9.63 cm, and 3.7 cm, respectively. Therefore, the plant height of the transgenic *Arabidopsis thaliana* plant overexpressing ELb was dramatically lower than the wild type plant.

EXAMPLE 3

ELb RNAi or Knock-out Mutation Increase Plant Height and Volume

In this example, the inventors prepared, starting with a plant variant that is an ELa T-DNA insertion mutant, ELb RNAi transgenic *Arabidopsis thaliana* plants (ELb RNAi/eLa) and *Arabidopsis thaliana* variant plants with ELb gene knocked out. After 10 days of growth of both plants, the effects of ELb RNAi or knock-out mutations on plant heights and volumes were observed, and compared with a wild type plant cultivated under the same condition as control.

Figure 2:
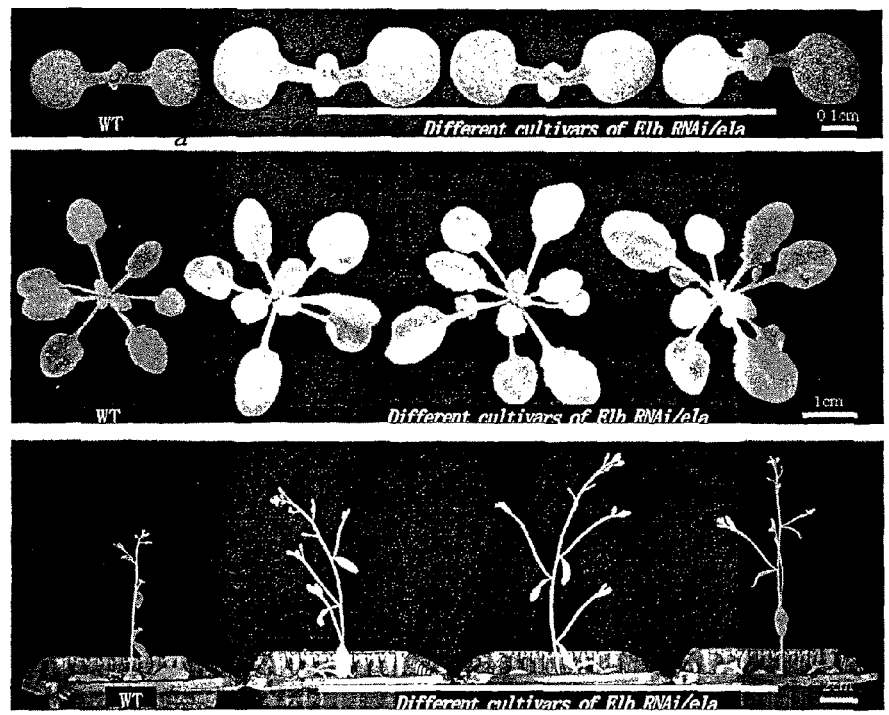
FIG. 2 shows a comparison of growth profiles between a wild-type (WT) *Arabidopsis* plant and ELb RNAi/ela *Arabidopsis* plants.

The growth profiles of the ELb RNAi/eLa plants and the wild type plant were shown in FIG. 2. In comparison with the wild type plant, the leaf areas, plant heights, and volumes of the ELb RNAi/eLa plants were dramatically increased.

Moreover, in comparison with the wild type plant, the leaf areas, plant heights, and volumes of ELb knock-out mutants (in the background of ELa T-DNA insertion) were also dramatically increased.

Accordingly, it can be concluded that decreased or silenced ELb expression leads to increased plant heights and volumes, i.e., ELb is a gene associated with decreased plant heights and volumes.

EXAMPLE 4

ELb RNAi/ela or Knock-out Mutantion Increase Flower Organ Sizes and Seed Sizes In this example, the inventor observed the growth profiles for flower organ and seed of the ELb RNAi/eLa *Arabidopsis thaliana* plants or the ELb knock-out *Arabidopsis thaliana* plants (generated in Example 3), and compare with the flower organs and seeds of a wild type *Arabidopsis thaliana* plant as controls.

Figure 3:
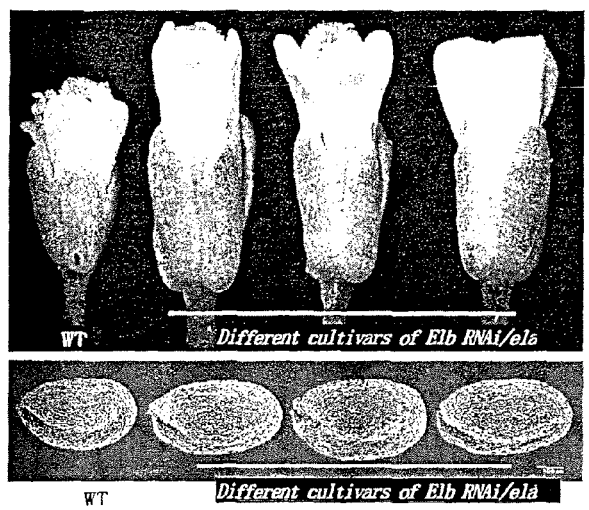
FIG. 3 shows a comparison of growth profiles of flower organs and seeds between Elb RNAi/ela *Arabidopsis* plants and a wild-type (WT) *Arabidopsis* plant.

The growth profiles for flower organs and seeds of the ELb RNAi/eLa *Arabidopsis thaliana* plants and a wild type *Arabidopsis thaliana* plant were shown in FIG. 3. The flower organs and seeds of the ELb RNAi/eLa *Arabidopsis thaliana* plant were significantly larger than those of the wild type plant.

Moreover, the flower organs and seeds of ELb knock-out mutant were also substantially larger than those of the wild type plant.

Accordingly, it can be concluded that decreased or silenced ELb expression leads to increased flower organ sizes and seed sizes of the plants, i.e., ELb is a gene associated with decreased flower organ sizes and seed sizes.

EXAMPLE 5

The Tissue-specific Expression of GUS Reporter Gene Initiated by ELb Promoter In this example, the inventor constructed a p ELb promoter:: GUS vector that could be transformed into *Agrobacterium tumefaciens* cells to prepare transgenic *Arabidopsis thaliana* plants. The expression of GUS reporter gene in the plants was observed by a conventional assay for detection of GUS reporter gene.

Figure 4:
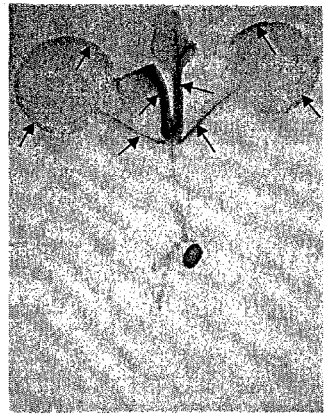
FIG. 4 shows tissue-specific expression of a reporter gene GUS initiated by the ELb promoter. The arrows indicate the regions displaying blue color.

The result was shown in FIG. 4. The GUS reporter gene was expressed in the eugonic of plant stems and leaves, but essentially not expressed in roots. Therefore, ELb gene is a tissue-specific gene.

EXAMPLE 6

Decreased Plant Height of ELb Over-expressing Transgenic Rice

In this example, the inventor prepared ELb over-expressing transgenic rice plants (ELb-OE) and observed the effect of ELb over-expression on rice plants. The wild-type rice plant TP309 cultivated in the same growth condition was used as control.

Figure 5:
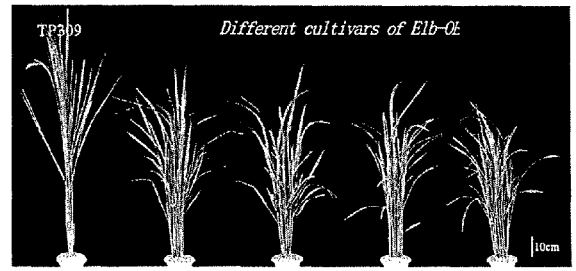
FIG. 5 shows a comparison of growth profiles between a wild-type rice (TP309) plant and Elb over-expressing rice (ELb-OE) plants.
Figure 6:
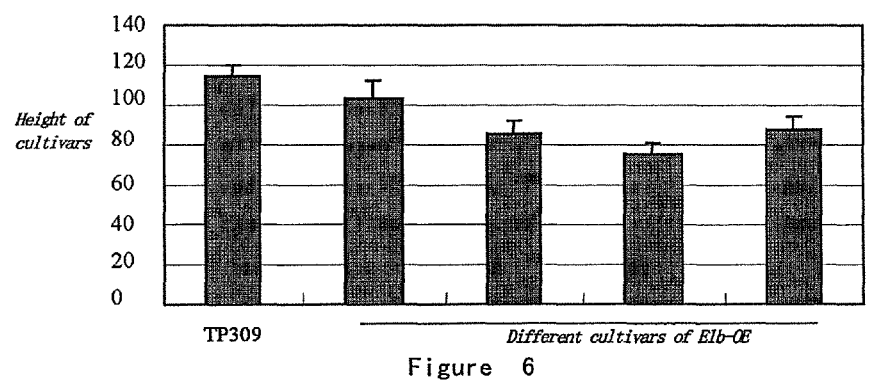
FIG. 6 shows statistical analysis of plant heights of a wild type rice (TP309) plant and Elb over-expressing rice (ELb-OE) plants.

After 110 days of growth, the growth profiles of the plants were shown in FIG. 5. It could be seen that the plant heights of ELb over-expressing transgenic rice plants were dramatically lower than the wild type plant. FIG. 6 is a statistical histogram showing the plant heights of the ELb over-expressing plants and the wild type plant.

EXAMPLE 7

Increased Effective Tillering Number and Yield of ELb Over-expressing Transgenic Rice In this example, the inventor detected the tillering number and yield of ELb over-expressing transgenic rice plants (ELb-OE) and the wild-type rice plant TP309 in order to demonstrate the effect of ELb over-expression on tillering and yield of the rice plants.

Figure 7:
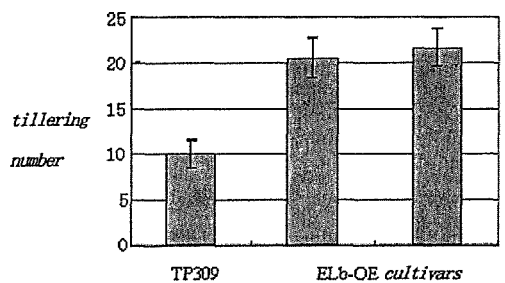
FIG. 7 shows statistical analysis of effective tillering numbers of a wild-type rice (TP309) plant and Elb over-expressing rice (ELb-OE) plants.

The effective tillers were counted after the cultivated plants tasseled, and the statistical results were shown in FIG. 7. The tillering number of the wild type plant was about 10, whereas the tillering numbers of ELb over-expressing plants were about 20-22. It can be concluded that ELb over-expression can dramatically increase the effective tillering numbers of the plants.

Figure 8:
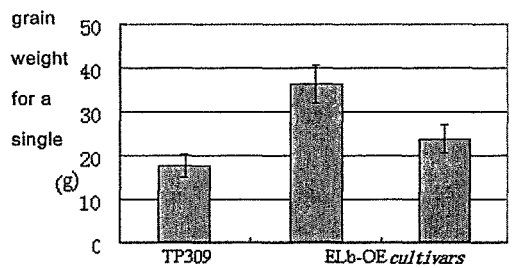
FIG. 8 shows a comparison of grain weights from a single plant between a wild-type rice (TP309) plant and Elb over-expressing rice (ELb-OE) plants.

The yields of the ELb over-expressing plants and the wild type plant were analyzed after maturation of the plants. The results were shown in FIG. 8. It can be concluded that the grain weights of a single plant for ELb over-expressing transgenic rice plants were dramatically increased.

EXAMPLE 8

The Function of ELb Variants

The ELb cDNA coding region in p35S::ELb vector was substituted by a coding sequence that encodes a protein having a sequence similar to SEQ ID NO:3, and the only difference is Leu at position 522 of the sequence as compared to Ile at the same position of the wild type ELb protein. This vector was transformed into *Agrobacterium tumefaciens* cells as described above to prepare the transgenic plants. The result showed that the plant heights of the transgenic plants were lower than the wild type plant.

All publications, patents, and patent applications cited herein are hereby incorporated by reference in their entirety as if each individual publication, patent, or patent application were individually indicated to be incorporated by reference. In addition, it is understood that various modifications or changes can be made by the persons skilled in the art in light of the content described herein, and these equivalents should also be included within the scope defined by the following claims in the application.

We claim

1. A method for decreasing plant height or volume, or increasing tillering or yield of a crop, comprising introducing and expressing in a plant a polynucleotide selected from the group consisting of:
   (a) a polynucleotide encoding a polypeptide having the amino acid sequence set forth in SEQ ID NO:3;
   (b) a polynucleotide encoding a variant of the polypeptide of (a), comprising substitution, deletion, or addition of 1-50 amino acid residues in the amino acid sequence set forth in SEQ ID NO:3 and wherein a plant transformed with said sequence has a decreased plant height,
   (c) the nucleotide sequence set forth in SEQ ID NO: 2: and
   (d) the nucleotide sequence set forth in SEQ ID NO: 1.

2. The method of claim 1, wherein said polynucleotide encodes the polypeptide having the amino acid sequence set forth in SEQ ID NO:3.

3. The method of claim 1, wherein said polynucleotide comprises:
the nucleotide sequence set forth in SEQ ID NO:1.

4. The method of claim 1, wherein said polynucleotide comprises the nucleotide sequence set forth in SEQ ID NO:2.

5. A method of producing a plant, wherein said method comprises the following steps:
(1) providing *Agrobacterium* carrying an expression vector containing a polynucleotide selected from the group consisting of: (a) a polynucleotide encoding a polypeptide having the amino acid sequence set forth in SEQ ID NO:3, (b) a polynucleotide encoding a variant of the polypeptide of (a), comprising substitution, deletion, or addition of 1-50 amino acid residues in the amino acid sequence set forth in SEQ ID NO:3 and wherein a plant transformed with said sequence has a decreased plant height, (c) the nucleotide sequence set forth in SEQ ID NO: 2, and (d) the nucleotide sequence set forth in SEQ ID NO: 1;
(2) contacting a cell, tissue, or organ of the plant with the *Agrobacterium* described in step (1), to introduce the polynucleotide into the cell, tissue, or organ and allow the polynucleotide to integrate into a chromosome of the cell, tissue, or organ;
(3) selecting the cell, tissue, or organ of the plant containing the polynucleotide; and
(4) allowing the cell, tissue, or organ of the plant described in step (3) to regenerate a new plant.

6. The method of claim 5, further comprising: crossbreeding the new plant with a non-transgenic plant, thereby obtaining a hybrid offspring containing the polynucleotide.

7. The method of claim 5, wherein the polynucleotide encodes the polypeptide having the amino acid sequence set forth in SEQ ID NO:3.

8. The method of claim 5, wherein the polynucleotide comprises
the nucleotide sequence set forth in SEQ ID NO:1.

9. The method of claim 5, wherein the polynucleotide comprises the nucleotide sequence set forth in SEQ ID NO:2.

10. A transgenic plant prepared by the method of claim 5.

11. The transgenic plant of claim 10, wherein the plant is one selected from the group consisting of a Gramineae plant, a Cruciferae plant, and a xylophyta plant.

12. The transgenic plant of claim 10, wherein the plant is selected from the group consisting of soybean, corn (maize), cotton, canola, sugar beet, alfalfa, rice, wheat, barley, rye, sorghum, sugarcane, sunflower, oilseed rape, and vegetables.

* * * * *